United States Patent
Leuchs et al.

(10) Patent No.: US 12,404,498 B2
(45) Date of Patent: Sep. 2, 2025

(54) OPTIMIZED PARVOVIRUS H-1 PRODUCTION

(71) Applicant: DEUTSCHES KREBSFORSCHUNGSZENTRUM STIFTUNG DES ÖFFENTLICHEN RECHTS, Heidelberg (DE)

(72) Inventors: Barbara Leuchs, Heidelberg (DE); Veronika Frehtman, Heidelberg (DE); Marcus Müller, Bad Rappenau (DE); Jean Rommelaere, Heidelberg (DE); Michael Dahm, Munich (DE); Ottheinz Krebs, Munich (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 778 days.

(21) Appl. No.: 17/542,721

(22) Filed: Dec. 6, 2021

(65) Prior Publication Data
US 2022/0169992 A1    Jun. 2, 2022

Related U.S. Application Data

(63) Continuation-in-part of application No. PCT/EP2020/066748, filed on Jun. 17, 2020.

(30) Foreign Application Priority Data

Jun. 17, 2019 (EP) .................................. 19180628

(51) Int. Cl.
 C12N 7/00    (2006.01)
 C12N 5/071    (2010.01)

(52) U.S. Cl.
 CPC ............. *C12N 7/00* (2013.01); *C12N 5/0686* (2013.01); *C12N 2750/14351* (2013.01); *C12N 2750/14352* (2013.01)

(58) Field of Classification Search
 CPC .................... C12N 7/00; C12N 5/0686; C12N 2750/14351; C12N 2750/14352
 See application file for complete search history.

(56) References Cited

U.S. PATENT DOCUMENTS

| 9,803,219 B2 * | 10/2017 | El-Andaloussi | ....... C12N 15/86 |
| 10,266,810 B2 * | 4/2019 | Leuchs | .................... C12N 7/00 |
| 11,193,112 B2 * | 12/2021 | Leuchs | .................... A61P 35/00 |
| 2013/0189265 A1 | 7/2013 | Salome et al. | |
| 2019/0203184 A1 * | 7/2019 | Leuchs | .................... C12N 7/00 |

FOREIGN PATENT DOCUMENTS

| WO | 2016/206807 A1 | 12/2016 |
| WO | 2018/054720 A1 | 3/2018 |
| WO | 2018/086791 A1 | 5/2018 |

OTHER PUBLICATIONS

Kestler et al. (Hum Gene Ther. Jul. 1, 1999;10(10):1619-32. doi: 10.1089/10430349950017626; referenced in IDS (Year: 1999).*
Chaves et al. (Chaves et al., [Updated Apr. 10, 2023]. In: StatPearls. Treasure Island (FL): StatPearls Publishing; Jan. 2024. Available from: https://www.ncbi.nlm.nih.gov/books/NBK557550 (Year: 2023).*
Martin Wisher (Cancer Gene Ther. Dec. 2002;9(12):1056-61. doi: 10.1038/sj.cgt.7700536; referenced in IDS (Year: 2002).*
Jurgen Kestler, et al., cis Requirements for the Efficient Production of Recombinant DNA Vectors Based on Autonomous Parvoviruses, Human Gene Therapy (Jul. 1, 1999) 10:1619-1632.
Guy Ungerechts, et al., Moving oncolytic viruses into the clinic: clinical-grade production, purification, and characterization of diverse oncolytic viruses, Molecular Therapy-Methods & Clinical Development (2016) 3, 16018, p. 1-12.
Martin Wisher, Review: Biosafety and product release testing issues relevant to replication-competent oncolytic viruses, Cancer Gene Therapy (2002) 9, 1056-1061.

* cited by examiner

*Primary Examiner* — Christopher M Babic
*Assistant Examiner* — Joel D Levin
(74) *Attorney, Agent, or Firm* — Duane Morris LLP; Thomas J. Kowalski

(57) ABSTRACT

The present invention provides a robust single clone Master Cell Bank (MCB) for an optimized production of H-1 parvovirus (H-1 PV) which is suitable to increase infectious parvovirus production compared to standard producer NB-324K mixed cells.

13 Claims, 6 Drawing Sheets

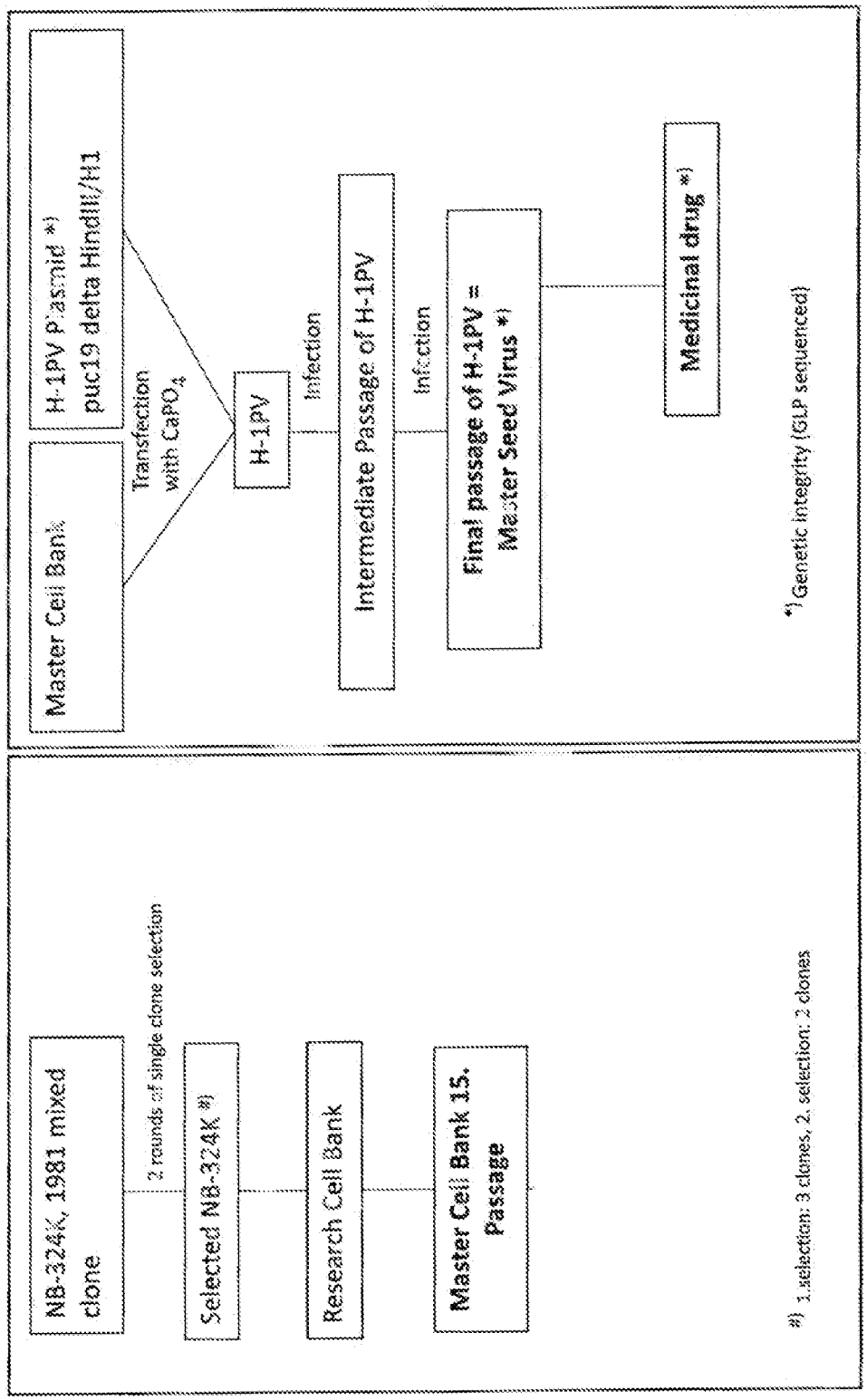
Figure 1: Generation of Master Cell Bank and Master Seed Virus for H-1PV Production.

OPTIMIZED PARVOVIRUS H-1 PRODUCTION

RELATED APPLICATIONS AND INCORPORATION BY REFERENCE

This application is a continuation-in-part of International application PCT/EP2020/066748 filed Jun. 17, 2020 and published as international publication WO 2020/254395 on Dec. 24, 2020, and which claims the benefit of priority from EP Patent Application EP 19180628.0 filed Jun. 17, 2019.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention provides a robust single clone Master Cell Bank (MCB) for an optimized production of H-1 parvovirus (H-1 PV) which is suitable to increase infectious parvovirus production compared to standard producer NB-324K mixed cells.

BACKGROUND OF THE INVENTION

H-1PV belongs to the genus Protoparvovirus within the Parvovirinae subfamily of Parvoviridae (Cotmore et al., 2014). It consists of a non-enveloped icosahedral capsid, 25 nm in diameter and contains a single-stranded DNA genome about 5 kb long, encoding non-structural proteins—notably NS1 (83 kDa) and NS2 (25 kDa)—and the capsid proteins VP1 (81 kDa) and VP2 (65 kDa). Another capsid protein, VP3 (63 kDa), is generated by post-translational cleavage of VP2 (Faisst et al., 1995; Halder et al., 2012; Hanson and Rhode, 1991; Toolan et al., 1960). Protoparvoviruses replicate in a S-phase-dependent fashion and undergo a lytic cycle after infection of permissive cells (Burnett et al., 2006). While the natural host of H-1PV is the rat, this virus has recently raised much interest because it replicates preferentially in transformed cells, including a number of human tumor cells. The virus has oncolytic and oncosuppressive properties that have been demonstrated in various cell cultures and animal models (Nuesch et al., 2012; Rommelaere et al., 2010). In xenograft models, H-1PV has been shown to suppress a number of human tumors, including cervical tumors (Faisst et al., 1998; Li et al., 2013), pancreatic tumors (Angelova et al., 2009b; Grekova et al., 2011), mammary carcinomas (Dupressoir et al., 1989), gliomas (Geletneky et al., 2010; Kiprianova et al., 2011), and lymphomas (Angelova et al., 2009a). On the basis of these preclinical proofs of concept, a first clinical trial (phase I/IIa) of H-1PV was launched in 2011, for patients with recurrent glioblastoma multiforme (Geletneky et al., 2012).

To test and eventually exploit the therapeutic potential of H-1PV, it is necessary to develop an efficient, simple, robust and reproducible virus production and purification process. Purification methods have been published for small-scale production by cesium chloride (Halder et al., 2012; Paradiso, 1981) or Iodixanol (Wrzesinski et al., 2003; Zolotukhin et al., 1999) density gradient centrifugation.

Oncolytic protoparvovirus research has reached the stage of transition into clinical practice, with a first phase I/IIa study of H-1PV in patients with recurrent resectable malignant glioma (Geletneky et al., 2012). In addition, a phase I/II clinical trial has been initiated in patients with inoperable metastatic pancreatic cancer (ClinicalTrials.gov Identifier: NCT02653313; manuscript in preparation).

These developments rely on the availability of robust procedures for protoparvovirus production and characterization. On the one hand, standardized procedures are needed to generate preclinical data that can provide the proof of concept. On the other hand, standard operating procedures are also required for the transfer of technologies and standards to the certified facilities in charge of producing clinical batches and establishing their specifications.

However, the use of well-characterized virus preparations and analytical methods is indeed a prerequisite for obtaining valid, reproducible evidence of the therapeutic efficacy of oncolytic protoparvoviruses in oncology and are required by regulatory authorities.

H-1PV production is routinely carried out in cell cultures, such as human newborn kidney cells NB-324K mixed cells (WO 2016/206807 A1).

However, there remains a need for new producer cells for H-1PV production which have higher mechanical stability, higher transfection efficiency resulting in higher productivity and higher robustness against ammonia in comparison to NB-324K mixed cells and resulting in more infectious H-1PV.

Citation or identification of any document in this application is not an admission that such document is available as prior art to the present invention.

SUMMARY OF THE INVENTION

The technical problem underlying the present invention is to optimize the parvovirus large scale production by single clone MCB cells.

The present invention relates to a process for preparing a single clone master cell bank (MCB) for parvovirus H-1PV production, which may comprise the following steps:
  (a) growing a NB-324K mixed clone in a cell culture medium,
  (b) seeding ideally 1 cell per well in a 96 well plate and growing it for 20-28 days,
  (c) choosing 2 to 5 cell clones obtained in step (b), in which the cells showed a single colony per well,
  (d) seeding at least two first round single clones in a 96 well as single cell/well for 20-23 days, and testing for growth and production,
  (e) propagating and passaging the selected single cell clone with the best growth and production properties until a passage higher than passage 15, and
  (f) harvesting and storing the obtained cells.

The present invention also relates to a process of preparing a master seed virus (MSV) composition which may comprise
  (a) providing a master cell bank obtained in any of paragraphs 1-3,
  (b) transfecting the master cell bank with sequenced pUC19ΔHindIII/H1 plasmid DNA (c) at least 2 rounds of infection of MCB cells with H-1PV plasmid DNA to generate the MSV.

The present invention also relates to a process for producing parvovirus H-1 (H-1PV), wherein said method may comprise:
(a) providing a master cell bank (MCB);
(b) Pre-seeding the MCB cells with the master seed virus (MSV) obtained in any of paragraphs 4 and 5,
(c) infecting the cells at a cell density from 2.0 to $5.0 \times 10^4$ cells/cm$^2$ with the MSV at a MOI of 0.5 to $5 \times 10^{-2}$ PFU/cells;
(d) growing the cells for about 2 to 6 days and harvesting the cells 2 to 6 days post-infection and obtaining a cell pellet by centrifugation;
(e) subjecting the resuspended cell pellet to a mechanical, physical or chemical cell lysis method for obtaining a parvovirus containing cell lysate;
(f) clarifying the parvovirus harvest by filtration; and
(g) subjecting it to DNAse treatment;
(h) buffer exchange for chromatography preparation;
(i) chromatography to eliminate empty particles and most impurities;
(j) buffer exchange and concentration through a desalting column or by a tangential flow filtration;
(k) final formulation in Visipaque/Ringer or other formulation solution.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposits

The Deposits with the DSMZ (=German Collection of Microorganisms and Cell Cultures), under deposit accession number DSM ACC3353 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: Generation of Master Cell Bank and Master Seed Virus for H-1PV Production.

The cells of NB-324K mixed clone underwent 2 rounds of single colony selection with MEM, 5% FBS, 2% L-Glutamine and 0.2% Gentamicin and the selected clone D8-G3 was used first for establishment of Research Cell Seed (RCS) followed by the establishment of Master Cell Bank (MCB; passage 15 or higher) for H1-PV production. For Master Seed Virus (MSV) generation single clone MCB cells were transfected with sequenced pUC19deltaHindII/H1 plasmid DNA. After two rounds of MCB cells infection with H-1PV, the final passage was defined as MSV. For medicinal production MCB Working cell bank cells are infected with MSV (or corresponding working seed virus (WSV)).

Figures 2A, 2B:
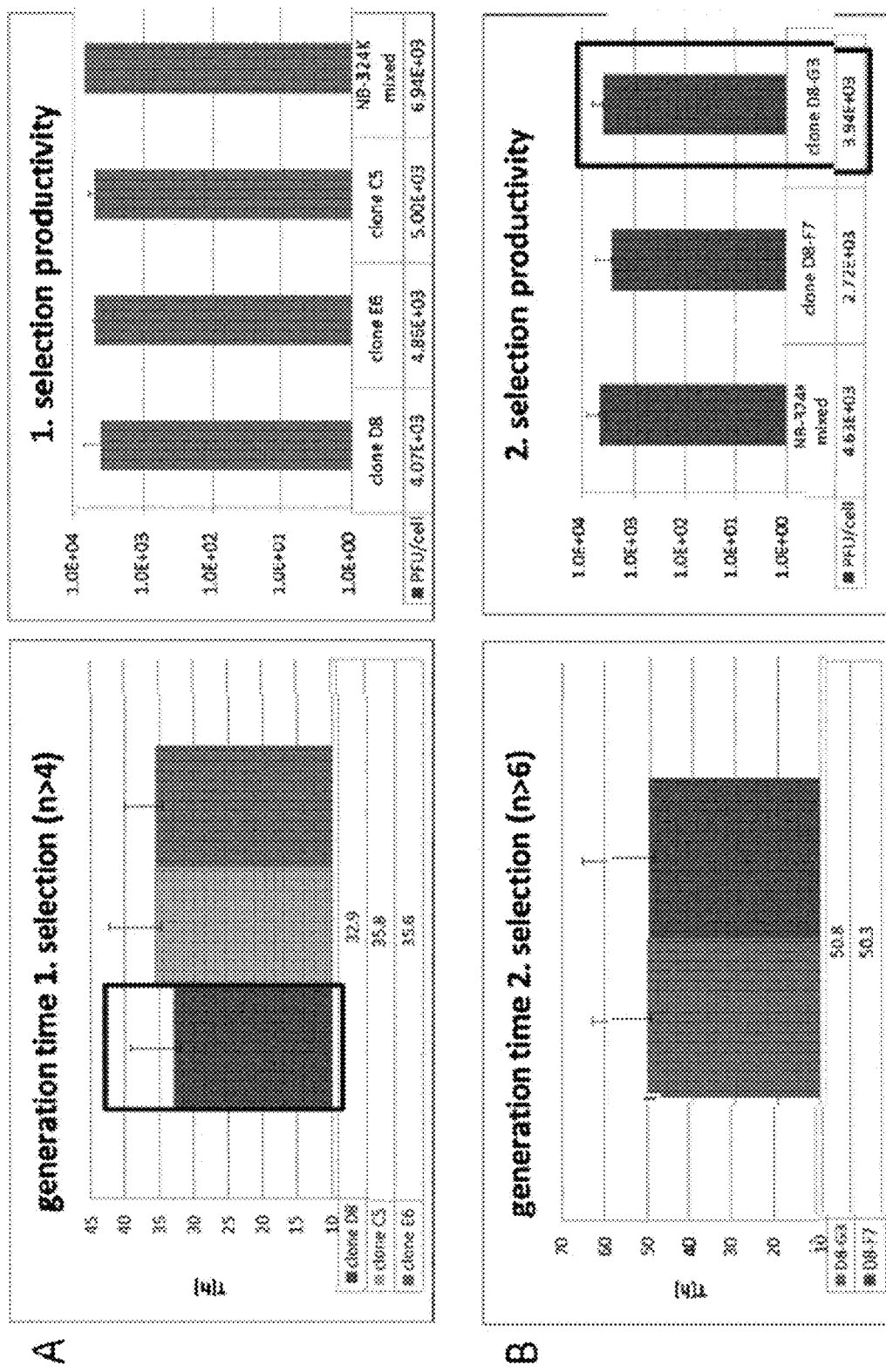

FIGS. 2A-2B: Two rounds of single cell clone selection for H-1PV GMP production.

First round of selection (A). Clone D8 (4.07 E+03±2.88 E+03 PFU/cell), clone E6 (4.86 E3±3.27 E+02 PFU/cell) and C5 (5.0 E+03±1.05 E+03 PFU/cell) (n=2) show same productivity that is comparable to NB-324K mixed clone (6.9 E3 PFU/cell). Furthermore, generation time of 3 selected clones (~33-35 h) is also similar to generation time of mixed clone NB-324K (~32 h; not shown) with clone D8 having the best generation time with 32.9 h. Consequently, it was decided to work with clone D8 in further experiments.

Second round of selection (B). The generation time of both mixed clones D8-G3 and D8-F7 is at 50 h. Productivity of clone D8-G3 is better than clone D8-F7 and similar to mixed clone NB-324K. Consequently, it was decided to establish research cell bank and master cell bank (MCB) with D8-G3 clone. The generation of the established MCB cell line is ~30 h and is used for the H-1PV production.

Figure 3:
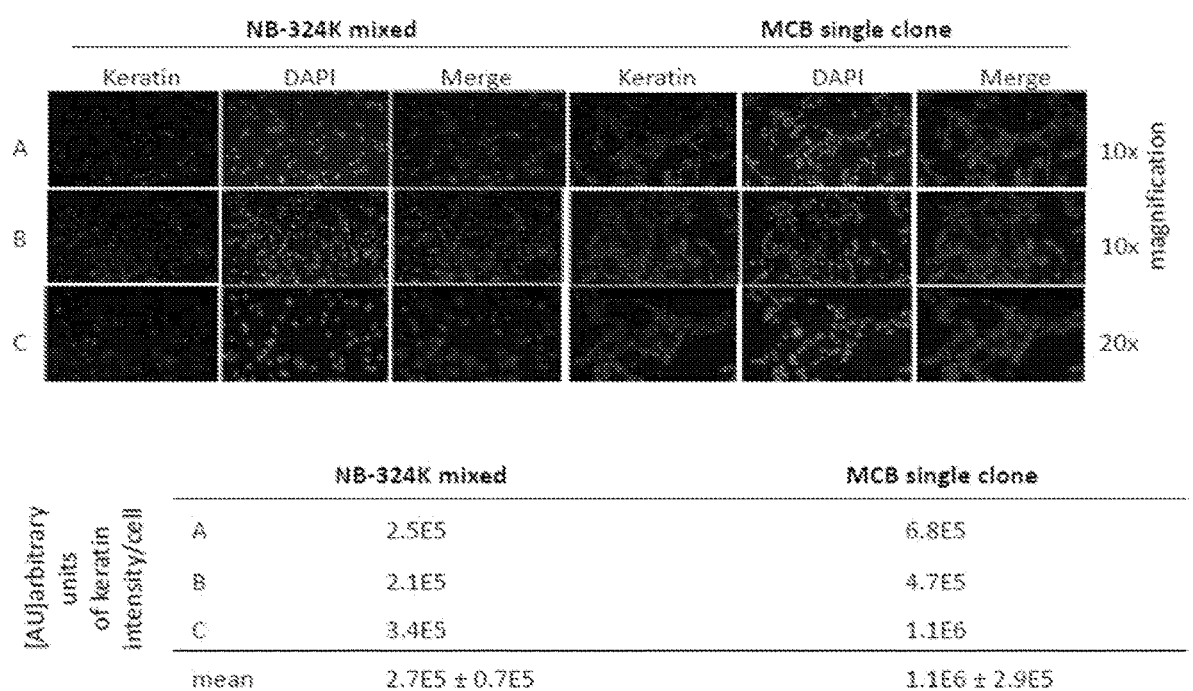

FIG. 3: Immunofluorescent comparison of mixed clone NB-324 and single clone MCB cells (A-C).

The NB-324K and MCB cells were stained with CH/HK keratin antibody that marks intermediate keratins and DAPI for nuclei staining. The nuclei count and total intensity assessment was performed with ImageJ software (imagej.nih.gov/ij/) and evaluated with a custom-developed macro (provided by Dr. Damir Krunic, DKFZ Light Microscopy Facility). Keratins play a major functional role in the integrity and mechanical stability of both the single epithelial cells and, via cell-cell contacts, of that of the epithelial tissues (Moll et al, 2008; The human keratins: biology and pathology, Histochem Cell Biol, 129:705-733). Single clone MCB cells demonstrate 2.7× higher keratin signal intensity/cell, implying higher mechanical stability of the single clone MCB cells compared to NB-324K mixed clone cells. This mechanical stability may play a role in a robust upscaling process.

Figure 4A:
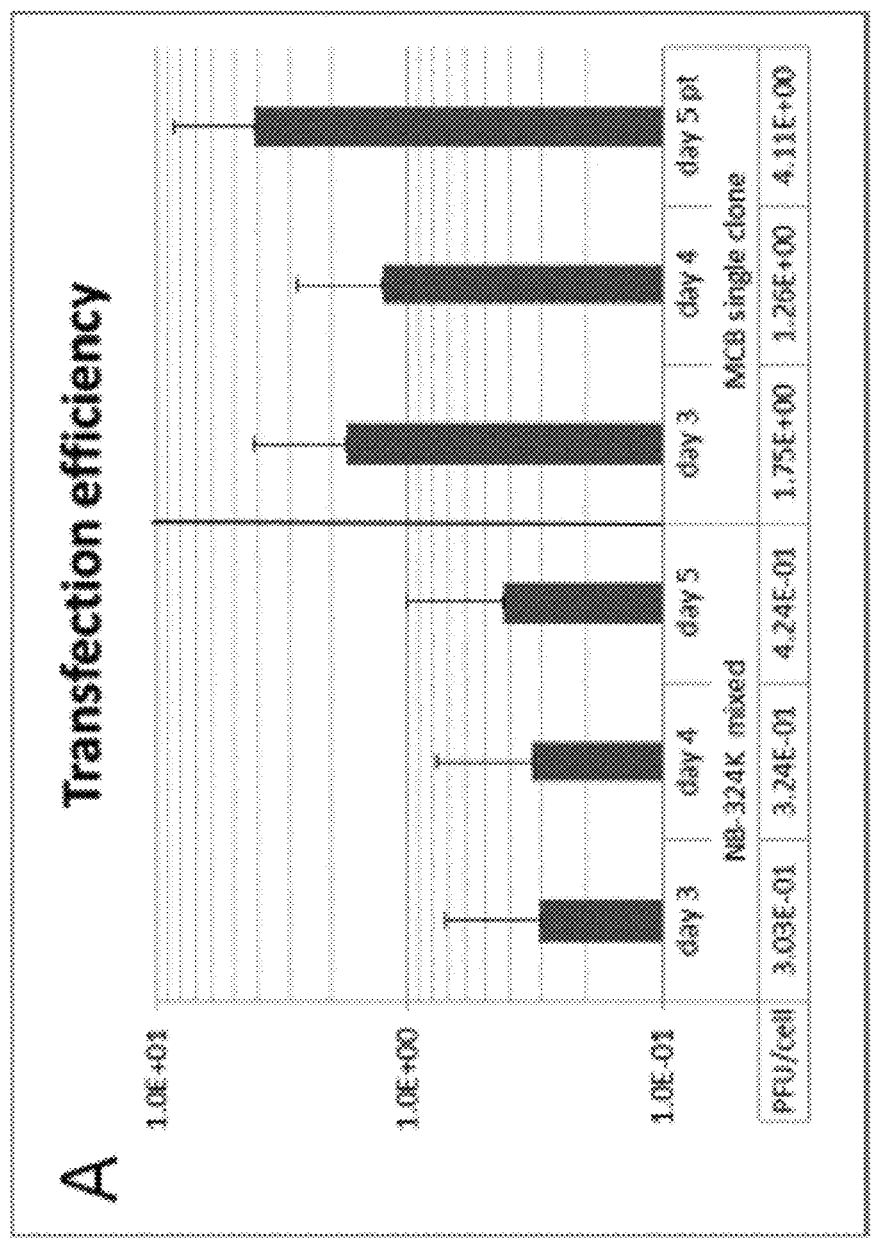
Figure 4B:
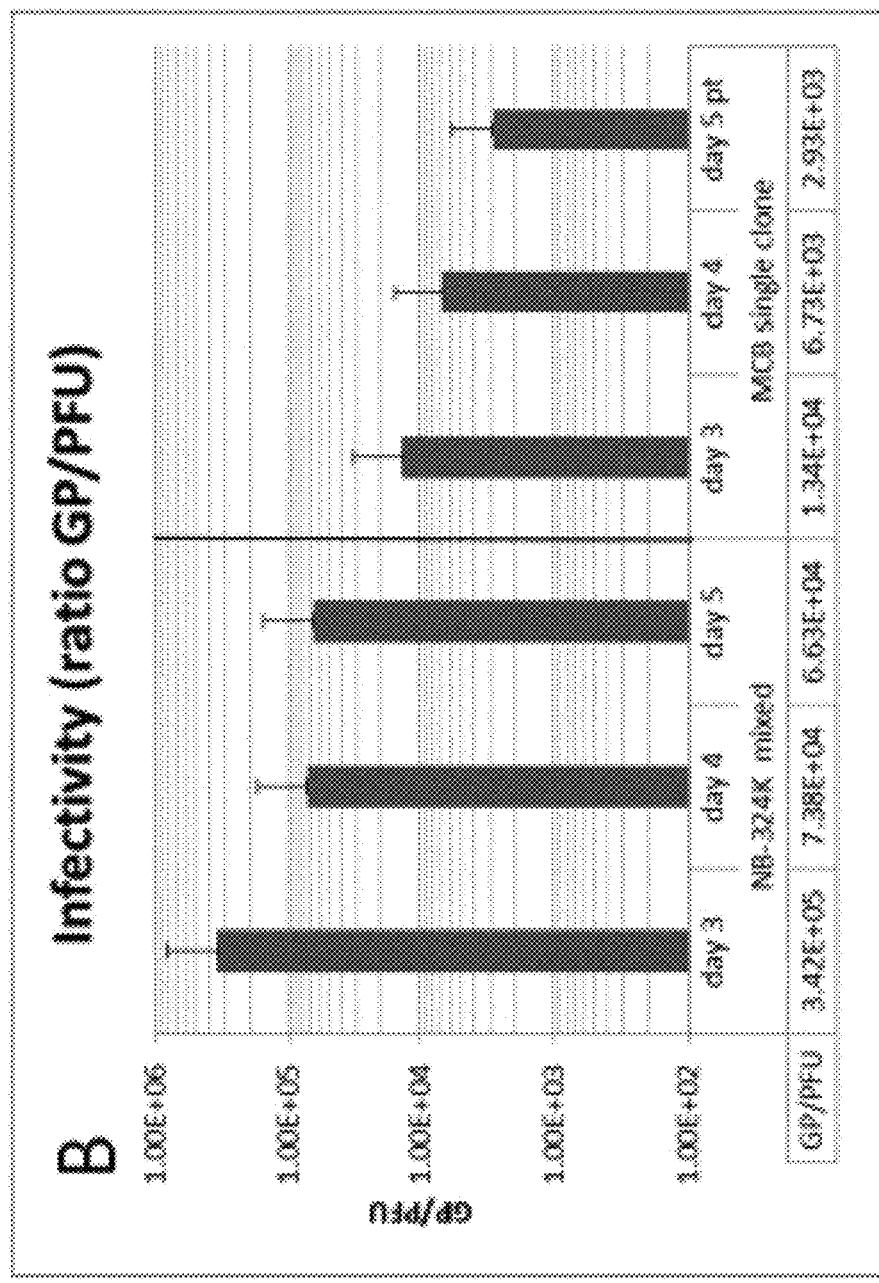

FIGS. 4A-4B: Higher transfection efficiency of single clone MCB cells.

The NB-324K and MCB cells were transfected with the H-1PV producing plasmid clone using the calcium phosphate method. The single clone MCB shows advantage with higher transfection efficacy compared to the mixed NB-324K cells (A). The genome containing particles to infectious particles ratio (GP/PFU) is lower with the single clone MCB (B), representing less defective particles and more infectious particles in the product.

Figure 5:
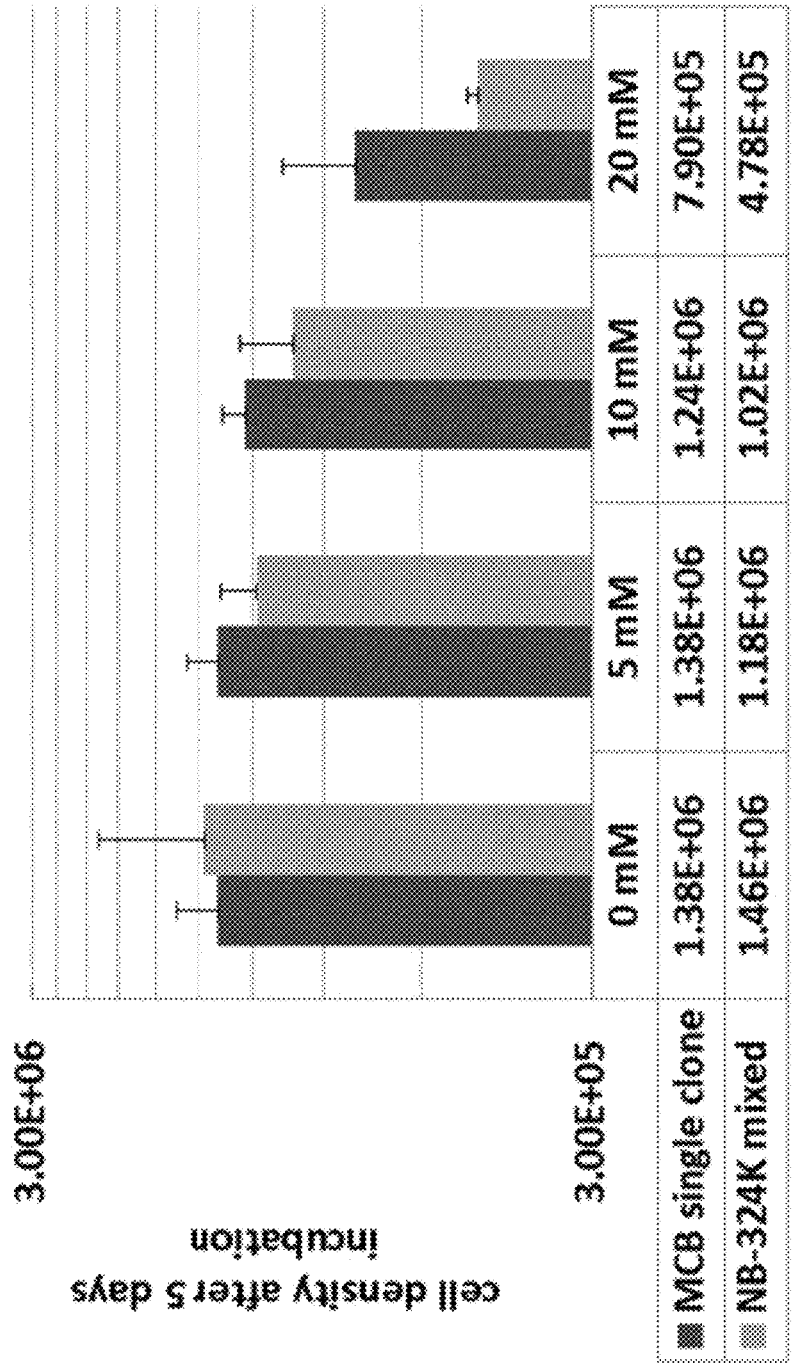

FIG. 5: High robustness against ammonia of single clone MCB cells in comparison to NB-324K mixed cells.

The cells were treated with different ammonia concentrations and counted after 5 days growth. The single clone MCB cells show a higher robustness up to 20 mM ammonia in comparison to the NB-324K mixed cells. This robustness demonstrates an advantage of MCB cells during the cell propagation and H-1PV production process since ammonia is the major product from glutamine metabolism. Its accumulation has been demonstrated to diminish growth and to negatively influence metabolism. Ammonia accumulation could disrupt electrochemical cell gradient and induce cytoplasm acidification. Furthermore, it could induce apoptosis in cultured cells (Cruz et al., 2000, "Effects of ammonia and lactate on growth, metabolism, and productivity of BHK cells"; Hassell et al., 1990, "Growth inhibition in Animal cell culture").

Cells of a particular preferred single cell MCB ("MCS NB324K human") have been deposited under Budapest Treaty with the German Collection of Microorganisms and Cell Cultures (DSMZ) in Braunschweig on May 16, 2019 under the accession number DSM ACC3353.

DETAILED DESCRIPTION OF THE INVENTION

The present invention relates to a process of preparing a single clone master cell bank (MCB) for parvovirus H-1PV production by growing NB-324K mixed clone (Shein & Enders, 1962; Solon L. Rhode, 1976; Tattersall and Bratton, 1983) in a suitable medium, preferably MEM medium containing fetal bovine serum (FBS), L-Glutamine and Gentamicin, under suitable conditions (e.g. 37° C., 5% CO2). The single cell cloning was generated by seeding 1 cell (in theory) per well in a 96 well plate for 20-28 days, preferably about 24 days. 2 to 5, preferably 3, cell clones, in which the cells showed a single colony per well and a fast propagation over the time were chosen in the beginning. They have been tested for good cell growth and productivity. Afterwards two first round single clones were seeded again in a 96 well as single cell/well for 20-23 days, preferably about 21 days, and tested again for growth and production. The best selected single cell clone was then propagated and passaged, e.g. in a T-Flask and Roller bottle, in a suitable medium under suitable conditions until passage 15 or more (e.g. passage 16, 17, 18, 19, 20, 21, 22, 23, 24, 25, 26, 27, 28, 29, 30, 31, 32, 33, 34, 35, 36, 37, 38, 39, 40, 41). The cells were harvested and cell suspension was filled up into cryo vials. The resulting MCB is specified according to the requirements of the Europaean Pharmacopoeia. This is necessary to ensure that the H-1PV production process conforms to GMP requirements and the final product satisfies quality requirements.

For optimal results, the "master cell bank" is characterized by (a) morphology, (b) a viability of at least 80%, (c) sterility (d) a passage number 15 (e) lack of mycoplasma and mycobacteria contamination, (f) lack of SV 40 production, (g) lack of extraneous agents, (f) lack of foreign virus contamination, (g) identity, (h) lack of tumorigenicity and (i) oncogenity The present invention also relates to a process of preparing a master seed virus (MSV) composition which may comprise
  (a) preparing a master cell bank from NB-324K mixed clone cells as described above;
  (b) transfecting the master cell bank with sequenced pUC19ΔHindII/H1 plasmid DNA (Kestler et al, 1999) by a suitable method (e.g. calcium phosphate transfection method; Graham and Van der Eb, 1973)
  (c) at least 2 rounds of infection of MCB cells with the H-1PV plasmid DNA to generate the MSV.

The present invention relates further to a method for producing a parvovirus H-1PV formulation, said method which may comprise:
  (a) providing the master cell bank as described above,
  (b) Pre-seeding the MCB cells
  (c) infecting the cells at a suitable cell density, e.g. from 2.0 to $5.0 \times 10^4$ cells/cm$^2$, with the master seed virus (MSV) at a suitable MOI, e.g. 0.5 to $5 \times 10^{-2}$ PFU/cells;
  (d) growing the cells for about 2 to 6 days and harvesting the cells 2 to 6 days post-infection and obtaining a cell pellet by centrifugation;
  (e) subjecting the resuspended cell pellet to a mechanical, physical or chemical cell lysis method for obtaining a parvovirus containing cell lysate;
  (f) clarifying the parvovirus harvest by filtration; and
  (g) subjecting it to DNAse treatment;
  (h) buffer exchange for chromatography preparation;
  (i) chromatography, e.g. anion exchange chromatography, to eliminate empty particles and most impurities;
  (j) buffer exchange and concentration through a desalting column or by a tangential flow filtration;
  (k) final formulation in Visipaque/Ringer or other formulation solution.

The term "cell culture" means the maintenance of cells in an artificial, in-vitro environment. The media of the present invention can be used to culture adherent NB-324K cells.

The term "cultivation" means the maintenance of cells in vitro under conditions that favor growth, differentiation or continued viability, in an active or quiescent state, of the cells.

The phrase "cell culture medium" refers to a nutritive solution for cultivating cells.

The term "cell bank" refers to a collection of appropriate containers whose contents are of uniform composition, stored under defined conditions. Each container represents an aliquot of a single pool of cells.

The term "master cell bank (MCB)" or "master cell seed (MCS)" (both terms may be used interchangeably) refers to a collection of cells of uniform composition derived from a single source. In particular, it is ScNB-324K (synonym: MCS NB 324K) that has been deposited with the German Collection of Microorganisms and Cell Cultures (DSMZ) under Budapest Treaty.

The person skilled in the art knows general conditions for growing the master cell line and for infecting the cells with the parvovirus. Usually, the cells are cultured at 37° C., e.g., in minimal essential medium (MEM) with heat-inactivated fetal bovine serum (e.g. FBS 5%) in a 5% $CO_2$ atmosphere. Preferably, the medium should be supplemented with antibiotics (e.g. penicillin, streptomycin, gentamycin) and/or nutrients, e.g. L-glutamine.

In a preferred embodiment of the present invention, the cell density is from $2.5 \times 10^3$ to $1 \times 10^5$ cells/cm$^2$.

In a further preferred embodiment of the method of the present invention, virus production is performed in a single use cell culture system, preferably a 10-layer CellSTACK® (CS) chamber. Further upscaling may be achieved with, e.g. a 40-layer CS chamber or a carrier system.

Preferably, for harvesting, the culture medium is aspirated and infected cells are treated with a suitable buffer and/or enzyme or detergent e.g. PBS-EDTA, Tris buffer, Tween or Trypsin. The detached cells and if applicable the medium supernatant are centrifuged for obtaining a cell pellet, preferably at 5,000×g, preferably for about 5 min or filtered. The person skilled in the art knows suitable mechanical, chemical or physical methods for releasing the parvovirus from the producer cells. Preferably, this can be done by freeze/thaw cycles, ultrasound treatment and/or enzyme/detergent treatment. The person skilled in the art also knows suitable methods for sonicating the cells and subsequent DNAse treatment. E.g., the cells can be sonicated at 30 to 70 W for a sufficient time and DNAse-treatment is carried out with 10-80 U/ml DNAse, usually at 37° C. for 10 to 60 min.

As mentioned above, the final H-1PV formulation is preferably in Visipaque/Ringer as a carrier. According to a preferred embodiment of the present invention, the carrier is iodixanol in Ringer solution that is prepared by mixing 73.62% VISIPAQUE™ 320 (GE Healthcare) with 26.38% Ringer solution. VISIPAQUE™ 320 (GE Healthcare) contains 652 mg/ml Iodixanol (=65.2% iodixanol) so that the iodixanol concentration after mixing with Ringer solution is 48%. "Iodixanol" is a synonym for "Visipaque" (for human injection use) or "Iodixanolum" (research grade). The IUPAC name is 5-[acetyl-[3-[N-acetyl-3,5-bis(2,3-dihydroxypropylcarbamoyl)2,4,6,-triiodoanilino]2-hydroxypropyl]amino]-1-N,3, N-bis(2,3-dihydroxypropyl)-2,4,6-triiodobenzene-1,3-dicarboxamide. The CAS number is 92339—11-2. It is also a well known contrast agent for CT imaging.

As shown in the following examples, the single clone MCB (ScNB-324K) demonstrates clear advantages over NB-324K mixed cells: the keratin is more profoundly expressed in single clone MCB cells resulting in higher mechanical stability, the transfection efficacy with MCB cells is greater resulting in higher infectious productivity and the single clone MCB cells are more robust against ammonia.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

The following examples are intended to illustrate, but not to limit the invention. While such examples are typical of those that might be used, other methods known to those skilled in the art may alternatively be utilized.

Example 1

Materials and Methods

A. Immune Fluorescence Test

The immune fluorescence test is based on the use of fluorescence-marked antibodies which bind to the specific antigen by which certain extra and intracellular structures can be proved. This principle is used for keratin staining with a CH/HK-Keratin antibody that marks intermediate keratins. For this, the single clone MCB (ScNB-324K) and NB-324K mixed cells were seeded on glass slides in 6 cm cell dish with 6 E5 (FIG. 3C) and 1.2 E6 (FIG. 3A, B) cells/dish. After 24-hour incubation time the cells on the slides were washed in PBS, fixed for 10 minutes in icecold methanol and afterwards 5 minutes in icecold acetone. For the keratin detection the slides were pre-blocked with PBS with 0.05% BSA and afterwards incubated with the CH/HK-Keratin antibody for 1 hour. Afterwards slides were washed in PBS with 0.1% Triton, before the second antibody Cy3gp (Dianova, Germany) was incubated for 1 hour. The unbound second antibodies were removed by triple washing in PBS with 0.1% Triton. The slides were dipped in Ethanol and were dried. The slides were embedded with Fluoromount™ slide mounting medium (SigmaAldrich, Germany) including 1 µg/ml DAPI (4',6-diamidino-2-phenylindole, SigmaAldrich, Germany), that stains the nucleus of the cells. The analysis occurred with the fluorescence microscope BZ-9000 (Keyence, Germany). The nuclei count and total intensity assessment was performed with ImageJ software (imagej.nih.gov/ij).

B. Cultivation, Transfection and Infection of Single Clone MCB and NB-324K Mixed Cells Single clone MCB (ScNB-324K) and NB-324K mixed cells are cultured at 37° C. in VP-SFM medium with 5% FBS and 4 mM L-glutamine. For the transfection single clone MCB and NB-324K mixed cells were seeded with 3.6 E4 cells/75 cm² flask in MEM medium with 5% FBS, 2 mM Glutamin, Pen/Strep and transfected with puc19ΔHindIII/H1 plasmid using calcium phosphate transfection method. The cells were harvested on day 3, 4 and 5.

For identification of toxic effect of ammonia on single clone MCB and mixed NB-324K, single clone MCB and mixed NB-324K cells were cultivated in Corning flask (25 cm² growing surface and 5 mL VP-SFM with 5% FBS and 4 mM Glutamine medium/flask) or Nunc flask (75 cm² growing surface and 10 mL VP-SFM with 5% FBS and 4 mM Glutamine medium/flask). Ammonium chloride (Pan Reac AppliChem, Germany) was added to the medium in different concentrations (0, 5, 10 and 20 mM, 1 flask for each setting). On day 5 each setting was counted with a Countess® Cell counter (Life Technologies, Germany).

For H-1PV production, NB-324K cells and Single clone MCB (ScNB-324K) were seeded at 3.6 E4 cells/cm² and infected immediately with H-1PV at a multiplicity of infection (MOI) of 0.01 plaque forming units (PFU) per cell. The infected cells were incubated for 4 days at 37° C. under 5% $CO_2$ until the cytopathic effect (CPE), measured as the percentage of dead and detached cells observed under a light microscope, reached at least 30%. Cell density and viability were measured by staining living cells with 0.4% trypan blue (Invitrogen™, Germany). Cells were counted with a Countess® Cell counter (Life Technologies, Germany) and morphology was microscopically observed.

For harvesting, the medium was aspirated and infected cells were treated with PBS/1 mM EDTA. The medium supernatant and detached cells were centrifuged for 5 min at 5,000×g. The pellet was washed with PBS, resuspended in Virus Tris/EDTA buffer, pH 8.7 (VTE) containing 0.05 M Tris HCl, 0.5 mM EDTA, and subjected to three freeze/thaw cycles. After centrifugation for 5 min at 5,000×g, cell debris was discarded. The cell lysate was then sonicated at 48 W for 1 min in a Sonorex Super 10 P ultrasonic homogenizer (Bandelin, Germany) and treated with DNAse (50 U/ml, Sigma, Germany) for 30 min at 37° C.

C. Plaque Formation Assay (PFU)

Plaque assays were done essentially as described by Tattersall and Bratton, 1983. NB-324K cells were grown in monolayer cultures in MEM medium containing 5% FBS, 100 µg/ml penicillin, 100 µg/ml streptomycin, and 2 mM L-glutamine. They were infected at 60% confluence with serial dilutions of H-1PV and incubated for 1 h at 37° C. Then the inoculum was replaced with a bacto-agar overlay (1.7% in MEM containing 5% FBS). On day four post-infection, living cells were stained for 18-24 h by addition of 0.02% toluylene red staining solution (Sigma, Germany) containing bacto-agar (Becton Dickinson, Germany). The dishes were incubated at 37° C. under 5% CO2. Plaque-forming units were counted 5 days post-infection on a light box and their concentration expressed in PFU/ml.

D. Determination of Genome Containing Particles (GP)

The number of genome-containing viral particles (GP) was determined by Q-PCR, essentially as described previously (Lacroix et al., 2010). Each well received 20 µl reaction mix containing 1× Premix Ex Taq™ (TaKaRa, France), 0.3 µM labeled NS1-TaqMan™ probe, each primer at 0.3 µM, and 3 µl template. Q-PCR was run in an QuantStudio 3 Real-Time PCR System and results were processed with the QuantStudio 3 Design and Analysis Software 1.4 (Applied Biosystems, Germany).

Example 2

Comparison of Productivity of Single Cell Clone for H-1PV GMP Production Selection A. First Round of Selection Clone D8 (4.07 E+03±2.88 E+03), clone E6 (4.86 E3 E+02±3.27 E+02) and C5 (5.0 E+03±1.05 E+03) (n=2) show same productivity that is comparable to NB-324K mixed clone (6.9 E3 PFU/cell). Furthermore, generation time of 3 selected clones (~33-35 h) was also similar to generation time of mixed clone NB-324K (~32 h; not shown). Clone D8 has the best generation time with 32.9 h.

Consequently, it was decided to work with clone D8 in the 2. selection round due to shorter generation time and similar productivity.

B. Second Round of Selection

The generation time of both mixed clones D8-G3 and D8-F7 is at 50 h. Productivity of clone D8-G3 is better than clone D8-F7 and similar to mixed clone NB-324K. Consequently, it was decided to generate a master cell bank (MCB) with D8-G3 clone. The generation of the established MCB cell line is ~30 h and is used for the H-1PV production.

Example 3

Comparison of Keratin Intensity of Mixed Clone NB-324K and Single Clone MCB Cells Immunofluorescent comparison of mixed clone NB-324 and single clone MCB cells (A-C).

The NB-324K and MCB cells were stained with CH/HK keratin antibody that marks intermediate keratins and DAPI for nuclei staining. The nuclei count and total intensity assessment was performed with ImageJ software (https://imagej.nih.gov/ij/). Single clone MCB cells (ScNB-324K) demonstrate 2.7× higher keratin signal intensity/cell, implying higher mechanical stability of the single clone MCB cells compared to mixed clone NB-324K cells.

Example 4

Measurement of H-1PV Transfection Efficiency of NB-324K and MCB Cells

A. The NB-324K and MCB cells were transfected with the H-1PV producing plasmid clone using the calcium phosphate method. The single clone MCB shows advantage with ~1 log higher transfection efficacy compared to the NB-324K mixed cells.

B. The genome containing particles to infectious particles ratio (GP/PFU) is lower (~1 log) with the single clone MCB (ScNB-324K) representing less defective particles and more infectious particles in the product.

Example 5

Influence of Ammonia on Mixed Clone NB-234K Single Clone MCB Cells

The cells were treated with different ammonia concentrations and counted after 5 days growth. The single clone MCB cells (ScNB-324K) show a higher robustness up to 20 mM ammonia in comparison to the NB-324K mixed cells. This robustness demonstrates an advantage of MCB cells during the cell propagation and H-1PV production process since ammonia is the major product of glutamine metabolism. Its accumulation has been demonstrated to diminish growth and to negatively influence metabolism. Ammonia accumulation could disrupt electrochemical cell gradient and induce cytoplasm acidification. Furthermore, it could induce apoptosis in cultured cells.

LIST OF REFERENCES

1. Angelova, A. L., Aprahamian, M., Balboni, G., Delecluse, H. J., Feederle, R., Kiprianova, I., Grekova, S. P., Galabov, A. S., Witzens-Harig, M., Ho, A. D., Rommelaere, J. and Raykov, Z., 2009a. Oncolytic rat parvovirus H-1PV, a candidate for the treatment of human lymphoma: In vitro and in vivo studies. Molecular therapy; The journal of the American Society of Gene Therapy 17, 1164-72.
2. Angelova, A. L., Aprahamian, M., Grekova, S. P., Hajri, A., Leuchs, B., Giese, N. A., Dinsart, C., Herrmann, A., Balboni, G., Rommelaere, J. and Raykov, Z., 2009b. Improvement of Gemcitabine-Based Therapy of Pancreatic Carcinoma by Means of Oncolytic Parvovirus H-1PV. Clinical Cancer Research 15, 511-519.
3. Burnett, E., Cotmore, S. F. and Tattersall, P., 2006. Segregation of a single outboard left-end origin is essential for the viability of parvovirus minute virus of mice. J Virol 80, 10879-83.
4. Cotmore, S. F., Agbandje-McKenna, M., Chiorini, J. A., Mukha, D. V., Pintel, D. J., Qiu, J., Soderlund-Venermo, M., Tattersall, P., Tijssen, P., Gatherer, D. and Davison, A. J., 2014. The family Parvoviridae. Archives of virology 159, 1239-47.
5. Dupressoir, T., Vanacker, J. M., Cornelis, J. J., Duponchel, N. and Rommelaere, J., 1989. Inhibition by parvovirus H-1 of the formation of tumors in nude mice and colonies in vitro by transformed human mammary epithelial cells. Cancer research 49, 3203-8.
6. Faisst, S., Faisst, S. R., Dupressoir, T., Plaza, S., Pujol, A., Jauniaux, J. C., Rhode, S. L. and Rommelaere, J., 1995. Isolation of a Fully Infectious Variant of Parvovirus H-1 Supplanting the Standard Strain in Human-Cells. Journal of Virology 69, 4538-4543.

7. Faisst, S., Guittard, D., Benner, A., Cesbron, J. Y., Schlehofer, J. R., Rommelaere, J. and Dupressoir, T., 1998. Dose-dependent regression of HeLa cell-derived tumours in SCID mice after parvovirus H-1 infection. International journal of cancer. Journal international du cancer 75, 584-9.
8. Fallon, A. E., Rozin, P., and Pliner, P., 1984. The child's conception of food: The development of food rejections with special reference to disgust and contamination sensitivity. Child Devel. 55: 566-575.
9. Geletneky, K., Huesing, J., Rommelaere, J., Schlehofer, J. R., Leuchs, B., Dahm, M., Krebs, O., von Knebel Doeberitz, M., Huber, B. and Hajda, J., 2012. Phase I/IIa study of intratumoral/intracerebral or intravenous/intracerebral administration of Parvovirus H-1 (ParvOryx) in patients with progressive primary or recurrent glioblastoma multiforme: ParvOryx01 protocol. BMC cancer 12, 99
10. Geletneky, K., Kiprianova, I., Ayache, A., Koch, R., Herrero, Y. C. M., Deleu, L., Sommer, C., Thomas, N., Rommelaere, J. and Schlehofer, J. R., 2010. Regression of advanced rat and human gliomas by local or systemic treatment with oncolytic parvovirus H-1 in rat models. Neuro-oncology 12, 804-14.
11. Grekova, S. P., Aprahamian, M., Daeffler, L., Leuchs, B., Angelova, A., Giese, T., Galabov, A., Heller, A., Giese, N. A., Rommelaere, J. and Raykov, Z., 2011. Interferon gamma improves the vaccination potential of oncolytic parvovirus H-1PV for the treatment of peritoneal carcinomatosis in pancreatic cancer. Cancer biology & therapy 12, 888-95.
12. Griffith, O. M., 2006. Practical Techniques for centrifugal separations. FiberLite, Piramon Technologies, Inc.
13. Halder, S., Nam, H. J., Govindasamy, L., Vogel, M., Dinsart, C., Salome, N., McKenna, R. and Agbandje-McKenna, M., 2012. Production, purification, crystallization and structure determination of H-1 Parvovirus. Acta crystallographica. Section F, Structural biology and crystallization communications 68, 1571-6.
14. Hanson, N. D. and Rhode, S. L., 3rd, 1991. Parvovirus NS1 stimulates P4 expression by interaction with the terminal repeats and through DNA amplification. J Virol 65, 4325-33.
15. Keay, L., 1975. Biotechnol. Bioengign. 17:745-764
16. Kiprianova, I., Thomas, N., Ayache, A., Fischer, M., Leuchs, B., Klein, M., Rommelaere, J. and Schlehofer, J. R., 2011. Regression of Glioma in Rat Models by Intranasal Application of Parvovirus H-1. Clinical Cancer Research 17, 5333-5342.
17. Kongsvik, J. R. and Toolan, H. W., 1972. Effect of proteolytic enzymes on the hemagglutinating property of the parvoviruses, H-1, H-3, and RV. Proceedings of the Society for Experimental Biology and Medicine. Society for Experimental Biology and Medicine 140, 140-4.
18. Lacroix, J., Leuchs, B., Li, J., Hristov, G., Deubzer, H. E., Kulozik, A. E., Rommelaere, J., Schlehofer, J. R. and Witt, O., 2010. Parvovirus H1 selectively induces cytotoxic effects on human neuroblastoma cells. International journal of cancer. Journal international du cancer 127, 1230-9.
19. Li, J., Bonifati, S., Hristov, G., Marttila, T., Valmary-Degano, S., Stanzel, S., Schnolzer, M., Mougin, C., Aprahamian, M., Grekova, S. P., Raykov, Z., Rommelaere, J. and Marchini, A., 2013. Synergistic combination of valproic acid and oncolytic parvovirus H-1PV as a potential therapy against cervical and pancreatic carcinomas. EMBO molecular medicine 5, 1537-55.
20. Nuesch, J. P., Lacroix, J., Marchini, A. and Rommelaere, J., 2012. Molecular pathways: rodent parvoviruses—mechanisms of oncolysis and prospects for clinical cancer treatment. Clin Cancer Res 18, 3516-23.
21. Paradiso, P. R., 1981. Infectious process of the parvovirus H-1: correlation of protein content, particle density, and viral infectivity. J Virol 39, 800-7.
22. Rommelaere, J., Geletneky, K., Angelova, A. L., Daeffler, L., Dinsart, C., Kiprianova, I., Schlehofer, J. R. and Raykov, Z., 2010. Oncolytic parvoviruses as cancer therapeutics. Cytokine & growth factor reviews 21, 185-95.
23. Toolan, H. W., Dalldore, G., Barclay, M., Chandra, S. and Moore, A. E., 1960. An Unidentified, Filtrable Agent Isolated from Transplanted Human Tumors. Proceedings of the National Academy of Sciences of the United States of America 46, 1256-8.
24. Tattersall, P., Bratton, J.; 1983. Reciprocal Productive and Restrictive Virus-Cell Interactions of Immunosuppressive and Prototype Strains of Minute Virus of Mice. GENE THERAPY 10:1619-1632
25. Solon L. Rhode; 1976. Replication Process of the Parvovirus H-1. JOURNAL OF VIROLOGY, May 1977, p. 446-458 Vol. 22, No. 2
26. Shein & Enders, 1962. Multiplication and Cytopathogenicity of Simian Vacuolatin Virus 40 in Cultures of Human Tissues. Proc. Soc. Exptl. Biol. & Med. 109: 495-500
27. Kestler, J., Neeb, B., Struyf, S., van Damme, J., Cotmore, S., D'Abramo, A., Tattersall, P., Rommelaere, J., Dinsart, C. and Cornelis, J.; 1999. Cis Requirements for the Efficient Production of Recombinant DNA Vectors Based on Autonomous Parvoviruses. GENE THERAPY 10:1619-1632
28. Graham, F. L., van der Eb, J.; 1973 A New Technique for the Assay of Infectivity of Human Adenovirus 5 DNA. VIROLOGY 52, 456-467 (1973)

The invention is further described by the following numbered paragraphs:

1. Process for preparing a single clone master cell bank (MCB) for parvovirus H-1PV production, comprising the following steps:
    (a) growing a NB-324K mixed clone in a cell culture medium,
    (b) seeding ideally 1 cell per well in a 96 well plate and growing it for 20-28 days,
    (c) choosing 2 to 5 cell clones obtained in step (b), in which the cells showed a single colony per well,
    (d) seeding at least two first round single clones in a 96 well as single cell/well for 20-23 days, and testing for growth and production,
    (e) propagating and passaging the selected single cell clone with the best growth and production properties until a passage higher than passage 15,
    (f) harvesting and storing the obtained cells.
2. The process of paragraph 1, wherein the cell culture medium of step (a) is MEM medium containing fetal bovine serum (FBS), L-Glutamine and Gentamicin.
3. The process of paragraph 1 or 2, wherein propagating and passaging of step (e) is carried out in T-flask and roller bottles.
4. A process of preparing a master seed virus (MSV) composition comprising
    (a) providing a master cell bank obtained in any of paragraphs 1-3,
    (b) transfecting the master cell bank with sequenced pUC19ΔHindIII/H1 plasmid DNA (c) at least 2 rounds of infection of MCB cells with H-1PV plasmid DNA to generate the MSV.

5. The process of paragraph 4, wherein the transfection in step (b) is made by calcium phosphate transfection.

6. A method for producing parvovirus H-1 (H-1PV), wherein said method:
(a) providing the master cell bank (MCB) obtained in any of paragraphs 1 to 3;
(b) Pre-seeding the MCB cells with the master seed virus (MSV) obtained in any of paragraphs 4 and 5,
(c) infecting the cells at a cell density from 2.0 to $5.0 \times 10^4$ cells/cm$^2$ with the MSV at a MOI of 0.5 to $5 \times 10^{-2}$ PFU/cells;
(d) growing the cells for about 2 to 6 days and harvesting the cells 2 to 6 days post-infection and obtaining a cell pellet by centrifugation;
(e) subjecting the resuspended cell pellet to a mechanical, physical or chemical cell lysis method for obtaining a parvovirus containing cell lysate;
(f) clarifying the parvovirus harvest by filtration; and
(g) subjecting it to DNAse treatment;
(h) buffer exchange for chromatography preparation;
(i) chromatography to eliminate empty particles and most impurities;
(j) buffer exchange and concentration through a desalting column or by a tangential flow filtration;
(k) final formulation in Visipaque/Ringer or other formulation solution.

7. The method of paragraph 6, wherein the chromatography in step (h) is anion exchange chromatography.

8. Single clone master cell bank (MCB) for parvovirus H-1 production obtainable by the method of any of paragraphs 1-3.

9. Single clone master cell bank of paragraph 8 comprising cells that have been deposited according to Budapest Treaty under the accession number DSM ACC3353 with the DSMZ (=German Collection of Microorganisms and Cell Cultures).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A MCS NB 324K cell; wherein cells designated MCS NB 324K that have uniform composition and are from a single source have been deposited with the German Collection of Microorganisms and Cell Cultures (DSMZ) under accession number DSM ACC3353.

2. A single clone master cell bank (MCB) for parvovirus H-1 production comprising MCS NB 324K cells of claim 1.

3. A process for preparing the single clone MCB of claim 2, comprising:
(a) growing a NB-324K mixed clone cell population in a cell culture medium,
(b) seeding cells from the mixed clone cell population of step (a) in a 96 well plate, 1 cell per well, and growing the cells so seeded for 20-28 days to obtain cell clones,
(c) from the cell clones of step (b), selecting 2 to 5 cell clones that exhibit a single colony per well,
(d) seeding cells from at least two cell clones selected in (c) in a 96 well plate, 1 cell per well, and growing the cells so seeded for 20-23 days to obtain cell clones,
(e) selecting a cell clone from step (d) based on growth and H-1 parvovirus production, and propagating and passaging cells of that clone for between 15 to 41 passages, and
(f) harvesting and storing cells obtained from the 15 to 41 passages of step (e).

4. The process of claim 3, wherein the cell culture medium of step (a) is a minimum essential medium (MEM) containing fetal bovine serum (FBS), L-Glutamine and Gentamicin.

5. The process of claim 3, wherein propagating and passaging of step (e) is carried out in T-flask or roller bottles.

6. The process of claim 4, wherein propagating and passaging of step (e) is carried out in T-flask or roller bottles.

7. A process of preparing a master seed virus (MSV) composition comprising at least two rounds of transfecting the cells of the single clone MCB of claim 2 with sequenced H-1 parvovirus DNA cloned into a plasmid pUC19 in which the HindIII site is deleted (pUC19ΔHindIII/H1 plasmid DNA), thereby generating the MSV.

8. The process of claim 7, wherein transfecting comprises calcium phosphate transfection.

9. A method for producing parvovirus H-1 (H-1PV) comprising:
(a) preparing a master seed virus (MSV) composition comprising at least two rounds of transfecting the cells of the single clone MCB of claim 2 with sequenced H-1 parvovirus DNA cloned into a plasmid pUC19 in which the HindIII site is deleted (pUC19ΔHindIII/H1 plasmid DNA), thereby generating the MSV;
(b) pre-seeding by infecting cells of the single clone MCB of claim 2 with virus of the MSV of step (a) at a cell density from 2.0 to $5.0 \times 10^4$ cells/cm$^2$ and a MOI of 0.5 to $5 \times 10^{-2}$ PFU/cells;
(c) growing the infected cells of step (b) for about 2 to 6 days;
(d) harvesting cells from the step (c) cells, 2 to 6 days post-infection, centrifuging the harvested cells, and obtaining from the centrifuging a cell pellet;
(e) resuspending the cell pellet of step (d) and subjecting the resuspended cell pellet to a mechanical, physical or chemical cell lysis method for obtaining a parvovirus containing cell lysate;
(f) clarifying the parvovirus containing cell lysate of step (e) by filtration;
(g) treating the clarified parvovirus containing cell lysate of step (f) with DNAse to obtain a treated clarified parvovirus containing cell lysate;
(h) performing chromatography preparation comprising buffer exchange on the treated clarified parvovirus containing cell lysate of step (g) to obtain a chromatography-prepared treated clarified parvovirus containing cell lysate;
(i) removing from the chromatography-prepared treated clarified parvovirus containing cell lysate of step (h) empty particles and impurities by a process comprising chromatography, to obtain a purified parvovirus containing lysate;
(j) performing buffer exchange on the purified parvovirus containing lysate of step (i) and concentrating product therefrom through a desalting column or by a tangential flow filtration process; and
(k) admixing the product of step (j) with a carrier.

10. The method of claim 9 wherein the carrier in step (k) comprises Ringer solution or an admixture of iodixanol and Ringer solution.

11. The method of claim 10 wherein the carrier in step (k) comprises an admixture of iodixanol and Ringer solution.

12. The method of claim 9, wherein the chromatography in step (h) is anion exchange chromatography.

13. The method of claim 11, wherein the chromatography in step (h) is anion exchange chromatography.

\* \* \* \* \*